(12) United States Patent
Heikenfeld

(10) Patent No.: US 12,085,576 B2
(45) Date of Patent: Sep. 10, 2024

(54) HYBRID ENZYMATIC APTAMER SENSORS

(71) Applicant: University Of Cincinnati, Cincinnati, OH (US)

(72) Inventor: Jason Charles Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 1025 days.

(21) Appl. No.: 16/956,879

(22) PCT Filed: Dec. 21, 2018

(86) PCT No.: PCT/US2018/067044
§ 371 (c)(1),
(2) Date: Jun. 22, 2020

(87) PCT Pub. No.: WO2019/126620
PCT Pub. Date: Jun. 27, 2019

(65) Prior Publication Data
US 2020/0319214 A1    Oct. 8, 2020

Related U.S. Application Data

(60) Provisional application No. 62/609,471, filed on Dec. 22, 2017.

(51) Int. Cl.
*G01N 33/74*     (2006.01)
*C12N 15/115*    (2010.01)

(52) U.S. Cl.
CPC ......... *G01N 33/743* (2013.01); *C12N 15/115* (2013.01); *G01N 2333/723* (2013.01);
(Continued)

(58) Field of Classification Search
None
See application file for complete search history.

(56) References Cited

U.S. PATENT DOCUMENTS

2004/0101477 A1   5/2004  Leyland-Jones
2008/0100279 A1   5/2008  Mohapatra et al.
(Continued)

FOREIGN PATENT DOCUMENTS

WO    02/090994 A2    11/2002
WO    2006/078660 A2  7/2006
(Continued)

OTHER PUBLICATIONS

Fernandez, Renny Edwin; et al; "Disposable aptamer-sensor aided by magnetic nanoparticle enrichment for detection of salivary cortisol variations in obstructive" Scientific Reports, 7, 2017 (Year: 2017).*

(Continued)

*Primary Examiner* — David W Berke-Schlessel
(74) *Attorney, Agent, or Firm* — Wood Herron & Evans LLP

(57) ABSTRACT

Devices and methods for sensing analytes in a solution sample are provided. The device includes a substrate, a conversion component configured to convert the analyte in the sample solution into a metabolite, and an aptamer sensor configured to measure a presence of the metabolite, the aptamer sensor located on the substrate.

13 Claims, 1 Drawing Sheet
Specification includes a Sequence Listing.

(52) U.S. Cl.
CPC .................. *G01N 2333/904* (2013.01); *G01N 2333/91194* (2013.01)

(56) References Cited

U.S. PATENT DOCUMENTS

2013/0252319 A1  9/2013  Jung et al.
2015/0247816 A1  9/2015  Bhansali et al.

FOREIGN PATENT DOCUMENTS

| WO | 2014/027964 A1 | 2/2014 |
| WO | 2015/001050 A2 | 1/2015 |
| WO | 2017/044494 A1 | 3/2017 |
| WO | 2017/164982 A1 | 9/2017 |

OTHER PUBLICATIONS

Sanvicens, Nuria; et al; "Biosensors for pharmaceuticals based on novel technology" Trends in Analytical Chemistry, 30, 541-553, 2011 (Year: 2011).*

European Patent Office, International Search Report and Written Opinion issued in corresponding PCT Application No. PCT/US2018/067044, mailed on Apr. 10, 2019, 15 pages.

Wang, C et al., "An aptameric graphene nanosensor for label-free detection of small-molecule biomarkers", Biosensors and Bioelectronics, vol. 71, Sep. 1, 2015, pp. 222-229, XPo55575767, Amsterdam, NL.

* cited by examiner

SEQUENCE LISTING

<160> NUMBER OF SEQ ID NOS: 1

<210> SEQ ID NO 1
<211> LENGTH: 44
<212> TYPE: DNA
<213> ORGANISM: Artificial Sequence
<220> FEATURE:
<223> OTHER INFORMATION: Synthetic -continued

```
<400> SEQUENCE: 1
ctgctctcgg gacgtggatt ttccgcatac gaagttgtcc cgag          44
```

HYBRID ENZYMATIC APTAMER SENSORS

CROSS-REFERENCE TO RELATED APPLICATIONS

This application is a U.S. National Phase Application and claims benefit of and priority to PCT Application No. PCT/US2018/067044 filed Dec. 21, 2018, which in turn claims the benefit of U.S. Provisional Application No. 62/609,471, filed Dec. 22, 2017. The disclosures of the aforementioned applications are incorporated herein by reference in their entireties.

BACKGROUND OF THE INVENTION

Monitoring of analytes using aptamer sensors is an attractive modality for chemical sensing and biosensing, but aptamer sensors can struggle to achieve low limits of detection for small analytes, particularly for small analytes that are not chemically diverse in their structure (e.g., uniformly hydrophobic or uniformly hydrophilic). New techniques are needed that can leverage aptamer technology to sense such molecules.

SUMMARY OF THE INVENTION

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably chemically change an analyte using an enzyme or other chemical process in a way that makes it easier to detect.

In an embodiment, a device for sensing an analyte in a sample solution is provided. The device includes a substrate, a conversion component configured to convert the analyte in the sample solution into a metabolite, and an aptamer sensor configured to measure a presence of the metabolite. The conversion component and the aptamer sensor are located on the substrate.

In another embodiment, a method of sensing an analyte in a fluid is provided. The method includes converting the analyte into a metabolite and then sensing the metabolite with an aptamer sensor to determine a presence of analyte in the fluid.

BRIEF DESCRIPTION OF THE DRAWINGS

The objects and advantages of the disclosed invention will be further appreciated in light of the following detailed descriptions and drawings in which.

DETAILED DESCRIPTION OF THE INVENTION

Embodiments of the disclosed invention apply to sensor devices and methods for measuring analyte concentrations. Further, embodiments of the disclosed invention may apply to sensing devices, which can take on forms including cassettes, cartridges, patches, bands, straps, portions of clothing, wearables, or any suitable mechanism that reliably brings sensing technology into proximity with a fluid with a target analyte in it.

Certain embodiments of the disclosed invention show sensors as simple individual elements. It is understood that many sensors may include features which are not captured in the description herein. Sensors are preferably electrical in nature, but may also include optical, chemical, mechanical, or other known biosensing mechanisms. Sensors can be in duplicate, triplicate, or more, to provide improved data and readings. Certain embodiments of the disclosed invention include sub-components of sensing devices for use in or with the device in various applications, which are known (such as a battery, antenna, adhesive), and for purposes of brevity and focus on inventive aspects, such components are not explicitly shown in the diagrams or described in the embodiments of the disclosed invention.

As used herein, "reversible sensor" means the sensor is able to measure both increasing and decreasing concentrations without any additional change in stimulus or environment for the sensor other than the change in the analyte concentration.

Figure 1:
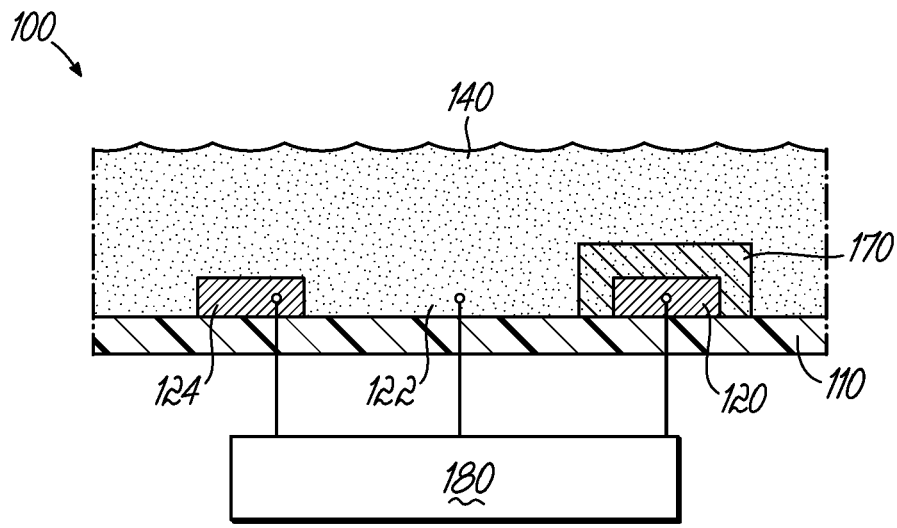
FIG. 1 is a cross-sectional view of a portion of a hybrid enzymatic/aptamer sensing device according to an embodiment of the disclosed invention in a fluid containing a target analyte.

With reference to FIG. 1, in an embodiment, a device 100 is capable of measuring an analyte of interest by converting the analyte of interest into a metabolite and measuring that metabolite. The devices and methods described herein may reduce a limit of detection of the analyte of interest by introducing hydrophilic moieties onto the chemical structure of the analyte of interest and increase the selectivity of sensing the analyte of interest.

With further reference to FIG. 1 the device 100 includes a sensor system with a working electrode or sensor 120, a counter electrode 122, and a reference electrode 124. The counter electrode 122 and reference electrode 124 may be made of, for example, gold. These electrodes 120, 122, 124 are connected to electronics 180 and carried on a substrate 110. The substrate 110 may include, for example, glass, plastic, or other inert durable material. The sensor 120 and electrodes 122, 124 are immersed in a sample solution 140. The sample solution 140 may be sweat, river water, or another fluid sample, that contains the analyte of interest. The sensor 120 includes and is housed within an enzyme coating 170, such as a hydrogel or porous matrix with an immobilized enzyme, for example enzymes utilized in glucose oxidase enzymatic sensors, to convert the analyte of interest into its metabolite, as discussed below.

In some examples of use of the device 100, the device 100 is worn by a user and the sample solution 140 is harvested directly from the user while the device 100 is being worn. In this way, it is possible for the sample solution 140 to be continuously supplied to the device so long as the user continues to generate the sample solution 140.

In another embodiment, the analyte of interest may be chemically converted into a form that is more easily detectable by the sensor 120 without enzymes by, for example, changing a pH or otherwise changing a solution/chemical environment in which the analyte of interest is included. In an embodiment, 100% of the analyte of interest is converted to the metabolite. Of note, the conversion process of the analyte of interest into the metabolite may be reversed such that the metabolite is converted into the analyte of interest. The sensor 120 is an aptamer sensor for the metabolite. As a result, the device 100 is able to detect the concentration of the analyte by converting it into the metabolite and detecting the metabolite with an aptamer. While example applications of the device 100 are described below, the disclosed invention is not so limited and extends to other analytes and conversion processes.

In an embodiment, the enzyme coating 170 is a coating of enzymes configured to convert an amount of the analyte of interest included in the sample solution 140 into a metabolite corresponding to the analyte of interest. The enzymes included in the enzyme coating 170 are selective to the analyte of interest and may be configured to avoid conversion of other analytes that may be present in the sample solution 140.

The analyte of interest may be, for example, cortisol. In an embodiment, the enzyme coating 170 is for converting cortisol to one of its metabolites, and the sensor 120 is an aptamer sensor for measuring that metabolite. Cortisol is metabolized by the 11-beta hydroxysteroid dehydrogenase system (11-beta HSD), which includes two enzymes: 11-beta HSD1 and 11-beta HSD2. 11-beta HSD1 uses the cofactor NADPH to convert biologically inert cortisone to biologically active cortisol, shown below.

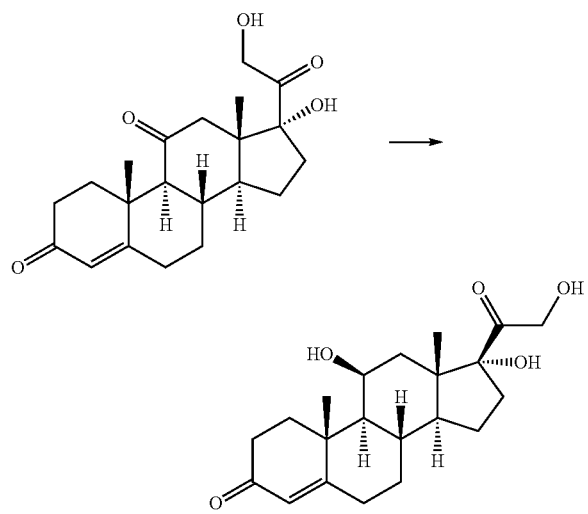

11-beta HSD2 uses the cofactor NAD+ to convert cortisol to cortisone. Overall, the net effect is that 11-beta HSD1 and 11-beta HSD2 serve to increase and decrease, respectively, the local concentration of biologically active cortisol in a given tissue.

Cortisol is also metabolized into 5-alpha tetrahydrocortisol (5-alpha THF) and 5-beta tetrahydrocortisol (5-beta THF), reactions for which 5-alpha reductase and 5-beta reductase are the rate-limiting factors, respectively. 5-beta reductase is also the rate-limiting factor in the conversion of cortisone to tetrahydrocortisone, shown below.

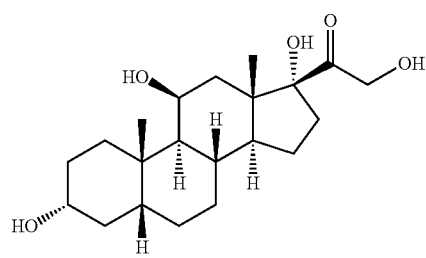

Thus, the enzyme coating 170 may include an enzyme for converting cortisol, or any analyte of interest, into one of its metabolites. In examples where the analyte of interest is cortisol, the cortisol may be converted into at least one of cortisone, 5-alpha THF, 5-beta THF, or tetrahydrocortisone. The device 100 is able to detect the concentration of the analyte of interest, for example cortisol, by converting it into one of its metabolites and detecting that metabolite with an aptamer.

In another embodiment, the analyte of interest is dehydroepiandrosterone (DHEA), also known as androstenolone, which is an endogenous steroid hormone. Dehydroepiandrosterone is one of the most abundant circulating steroids in humans, in whom it is produced in the adrenal glands, the gonads, and the brain, where it functions as a metabolic intermediate in the biosynthesis of the androgen and estrogen sex steroids. However, DHEA also has a variety of potential biological effects in its own right, binding to an array of nuclear and cell surface receptors, and acting as a neurosteroid and neurotrophin. Metabolites of DHEA include DHEA-S, 7α-hydroxy-DHEA, 7β-hydroxy-DHEA, 7-keto-DHEA, 7α-hydroxyepiandrosterone, and 7β-hydroxyepiandrosterone, as well as androstenediol and androstenedione. For example, DHEA is transformed into DHEA-S, as shown below, by sulfation at the C3β position via the sulfotransferase enzymes SULT2A1 and, to a lesser extent, SULT1E1.

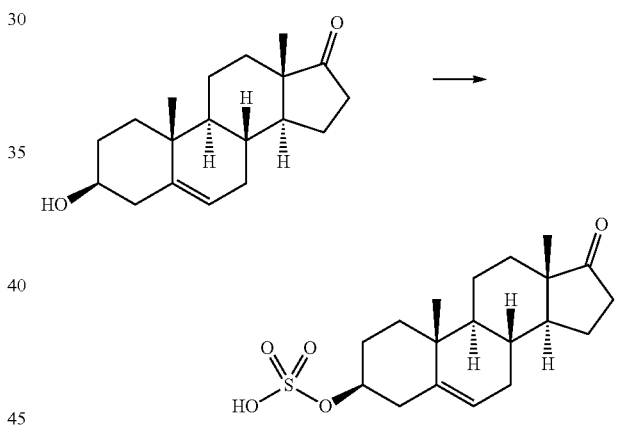

This occurs naturally in the adrenal cortex and during first-pass metabolism in the liver and intestines when exogenous DHEA is administered orally. Levels of DHEA-S in circulation are approximately 250 to 300 times those of DHEA. DHEA-S in turn can be converted back into DHEA in peripheral tissues via steroid sulfatase (STS). The terminal half-life of DHEA is short at only 15 to 30 minutes. In contrast, the terminal half-life of DHEA-S is far longer at 7 to 10 hours. Because DHEA-S can be converted back into DHEA, it serves as a circulating reservoir for DHEA, thereby extending the duration of DHEA.

With reference again to FIG. 1, in an embodiment, the enzyme coating 170 is for converting an analyte of interest into a metabolite, for example DHEA to DHEA-S, and the sensor 120 is an aptamer sensor for measuring the metabolite, for example DHEA-S. Suitable aptamer sensors for measuring the metabolite, for example DHEA-S, include, without limitation, those described by Wang et al., "An Aptameric Graphene Nanosensor for Label-Free Detection of Small-Molecule Biomarkers," Biosensors and Bioelectronics, Vol. 71, pp. 222-229 (2015), such as: PASE linker from Life Technologies (now Thermo Fisher Scientific Corp.); DNA aptamer of DHEA-S, the selective sequence being 5'-CTG CTC TCG GGA CGT GGA TTT TCC GCA TAC GAA GTT GTC CCG AG-3' (e.g., as described in Yang et al., "Optimizing Cross-reactivity with Evolutionary Search for Sensors," J Am Chem Soc. 2012; 134(3):1642-1647 (2012)); and 5'-amino group modified DNA anchor (selective sequence 5'-NH2-GTC CCG AG-3') from Integrated DNA Technologies (Coralville, IA). Thus, the device 100 is able to detect the concentration of the analyte, for example DHEA, by converting it into the metabolite, for example DHEA-S, and detecting the metabolite, for example DHEA-S, with the sensor 120.

The substrate 110 is any material suitable for supporting the sensor 120 and is typically a solid and inert material. Exemplary substrates 110 may be made of glass or polyethylene terephthalate (PET).

The sensor 120 is capable of detecting the metabolite of the analyte of interest, herein referred to as a metabolite. The metabolite is converted from the analyte of interest included in the sample solution 140. The sensor 120 is a reversible sensor. The sensor 120 is able to measure both increasing and decreasing concentrations without any additional change in stimulus or environment for the sensor 120 other than the change in the analyte concentration. In some examples, the sensor 120 may include an electrochemical sensor such as enzymatic, aptamer with a redox tag, impedimetric, or other types of sensors. The sensor is located on and supported by the substrate 110 and is housed by the substrate 110 in combination with the enzyme coating 170. In addition, the sensor 120 is configured to continuously detect the metabolite of the analyte of interest during operation of device 100.

Electrode 122, may be for example, a counter electrode of silver, silver chloride, gold, carbon, polyethylenedioxythiophene (PEDOT), or other materials suitable to function as an electrode. In some examples, the electrode 122 is paired with the sensor 120 to complete a circuit. Alternatively or in addition, electrode 122 may be paired with electrode 124 to complete a circuit. The circuit could be any electronics utilized to power the sensor 120, operate and read measurements from the sensor 120, or to alter the sensor 120 functionality in some way, including voltametric, impedimetric, amperometric, square wave voltammetry, or other suitable sensor measurement modalities.

Electrode 124, may be for example, a reference electrode of silver, silver chloride, gold, carbon, polyethylenedioxythiophene (PEDOT), or other materials suitable to function as an electrode. In some examples, the electrode 124 is paired with the sensor 120 to complete a circuit. Alternatively or in addition, electrode 124 may be paired with electrode 122 to complete a circuit. The circuit could be any electronics utilized to power the sensor 120, operate and read measurements from the sensor 120, or to alter the sensor 120 functionality in some way, including voltametric, impedimetric, amperometric, square wave voltammetry, or other suitable sensor measurement modalities.

The electronics 180 supply electrical power to the sensor 120 and electrodes 122, 124. The electronics 180 are in electrical communication with the sensor 120 and the electrodes 122, 124. In some examples, the electronics 180 communicate electrically with the sensor 120 and the electrodes 122, 124 via conductive wires. Alternatively or in addition, in some examples, the electronics 180 communicate electrically with the sensor 120 and the electrodes 122, 124 via antenna signaling. The electrical power supplied by the electronics 180 may be supplied in direct current or alternating current.

Figure 2:
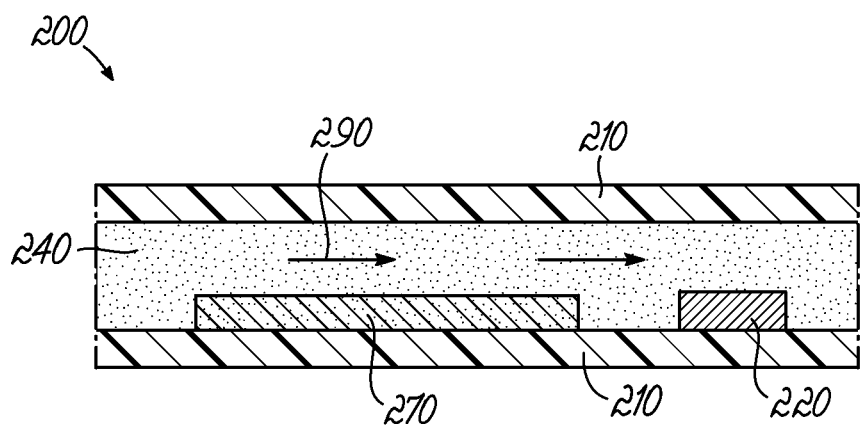
FIG. 2 is a cross-sectional view of a portion of a hybrid enzymatic/aptamer sensing device according to an embodiment of the disclosed invention a fluid channel containing a target analyte.

With reference to FIG. 2, where like numerals refer to like features in FIG. 1, a device 200 is capable of converting an analyte of interest into a metabolite and measuring that metabolite in a fluid channel defined by two substrates 210. The two substrates 210 form a channel through which a sample solution 240 may flow. The sample solution 240 including the analyte of interest flows in the direction of arrow 290 in the channel. In some examples, the sample solution 240 flows across an enzyme or chemical matrix 270 and then across a sensor 220. The enzyme or chemical matrix 270 converts the analyte of interest (e.g., cortisol) into a metabolite (e.g., tetrahydrocortisone), and sensor 220 is an aptamer sensor for measuring that metabolite. As the sample solution 240 flows through the channel, the analyte of interest is converted into its metabolite by the matrix 270 upstream of the sensor 220. As the sample solution 240 continues to flow downstream, the sensor 220 measures the metabolite.

In some examples of use of the device 200, the device 200 is worn by a user and the sample solution 240 is harvested directly from the user and proceeds to enter the channel while the device 200 is being worn. In this way, it is possible for the sample solution 240 to be continuously supplied to the device so long as the user continues to generate the sample solution 240.

The substrates 210 are any material suitable for supporting the sensor 220 and the enzyme or chemical matrix 270 and is typically a solid and inert material. Exemplary substrates 210 may be made of glass or polyethylene terephthalate (PET).

In an embodiment, the enzyme or chemical matrix 270 is a cluster of enzymes configured to convert an amount of the analyte of interest included in the sample solution 240 into a metabolite corresponding to the analyte of interest. The enzymes included in the enzyme or chemical matrix 270 are selective to the analyte of interest and may be configured to avoid conversion of other analytes that may be present in the sample solution 240. As a general term, the enzyme or chemical matrix 270 as well as the enzyme coating 170 (shown in FIG. 1) are considered a conversion component.

In some examples, the enzyme or chemical matrix 270 is positioned on only one of the substrates 210. In another example, the enzyme or chemical matrix 270 spans a cross section of the channel and is positioned on both substrates 210 (not shown). In some examples, the enzyme or chemical matrix 270 is an enzyme cluster. In other examples, the enzyme or chemical matrix 270 is a sheet or membrane that allows the sample solution 240 to permeate in the enzyme or chemical matrix 270 in the channel.

The sensor 220 is capable of detecting the metabolite of the analyte of interest, herein referred to as a metabolite. The metabolite is converted from the analyte of interest included in the sample solution 240. The sensor 220 is a reversible sensor. The sensor 220 is able to measure both increasing and decreasing concentrations without any additional change in stimulus or environment for the sensor 220 other than the change in the analyte concentration. In some examples, the sensor 220 may include an electrochemical sensor such as enzymatic, aptamer with a redox tag, impedimetric, or other types of sensors. The sensor is located on and supported by the substrate 210 and is housed by the substrates 210 and is located in the channel downstream of the enzyme or chemical matrix 270. In addition, the sensor 220 is configured to continuously detect the metabolite of the analyte of interest during operation of device 200.

The present invention may also be utilized to detect concentrations of drug molecules. For example acetaminophen (N-acetyl-p-aminophenol, APAP, or paracetamol, PARA) is widely used for its analgesic and antipyretic properties in many over-the-counter formulations in both adults and children, and is metabolized in the liver. The pathways for metabolizing acetaminophen are known, as taught by "PharmGKB summary: Pathways of acetaminophen metabolism at the therapeutic versus toxic doses," Pharmacogenet Genomics. 2015 August; 25(8): 416-426, doi: 10.1097/FPC.0000000000000150. In adults, the primary metabolic pathway for paracetamol is glucuronidation. A small amount of the drug is metabolized via the cytochrome P-450 pathway (to be specific, CYP3A4 and CYP2E1) into NAPBQI (N-acetyl-p-benzoquinone imine) These metabolic pathways and/or enzymes can be utilized in the present invention. It is further important to note, that in many cases the metabolic pathway includes additional solutes or chemicals to drive the metabolism, which are included within the spirit of the present invention and can comprise a conversion component that is configured to convert the analyte in the sample solution into a metabolite.

While the embodiments described above involve electrochemical sensing, embodiments of the disclosed invention are readily extendable to known aptamer approaches for optical or mechanical sensing as well.

The subject-matter of the disclosure may also relate, among others, to the following aspects:

1. A device for sensing an analyte in a sample solution comprising:
   a substrate;
   a conversion component configured to convert the analyte in the sample solution into a metabolite, the conversion component positioned on the substrate;
   an aptamer sensor configured to measure a presence of the metabolite, the aptamer sensor located on the substrate.
2. The device of aspect 1, wherein the conversion component is a source of enzymes, the enzymes configured to metabolize the analyte.
3. The device of aspect 1, wherein the conversion component is a metabolic pathway, the metabolic pathway configured to metabolize the analyte.
4. The device of any of aspects 1 to 3, wherein the analyte comprises a steroid hormone.
5. The device of any of aspects 1 to 3, wherein the analyte comprises a drug molecule.
6. The device of any of aspects 1 to 3, wherein the metabolite comprises at least one of cortisone, 5-alpha THF, 5-beta THF, or tetrahydrocortisone.
7. The device of any of aspects 1 to 6, wherein the conversion component comprises at least one of 11-beta HSD1 or 11-beta HSD2.
8. The device of any of aspects 1 to 7, further comprising an electronical supply in electrical communication with the aptamer sensor, the electrical supply configured to supply electrical power to the aptamer sensor.
9. The device of any of aspects 1 to 8, wherein the aptamer sensor is housed by the conversion component and the substrate.
10. The device of any of aspects 1 to 9, further comprising a fluid channel, wherein the conversion component and aptamer sensor are located in the fluid channel, the conversion component being upstream of the aptamer sensor.
11. The device of any of aspects 1 to 9, wherein the conversion component is a coating placed on or adjacent to the aptamer sensor that is located in the fluid channel.
12. The device of any of aspects 1 to 11, wherein the analyte comprises dehydroepiandrosterone.
13. The device of any of aspects 1 to 12, wherein the conversion component comprises sulfotransferase enzymes.
14. The device of any of aspects 1 to 13, wherein the metabolite comprises at least one of DHEA-S, 7α-hydroxy-DHEA, 7β-hydroxy-DHEA, 7-keto-DHEA, 7α-hydroxyepiandrosterone, 7β-hydroxyepiandrosterone, androstenediol, or androstenedione.
15. The device of any of aspects 1 to 14, wherein the terminal half-life of the metabolite is between 7 to 10 hours, inclusively.
16. A method of sensing an analyte in a fluid comprising:
   converting the analyte into a metabolite; and
   sensing the metabolite to determine a presence of the analyte in the fluid.
17. The method of aspect 16, wherein the analyte comprises cortisol.
18. The method of any of aspects 16 to 17, wherein the metabolite comprises at least one of cortisone, 5-alpha THF, 5-beta THF, or tetrahydrocortisone.
19. The method of any of aspects 16 to 18, wherein converting the analyte comprises enzymatically converting the analyte with an enzyme, the enzyme comprising at least one of 11-beta HSD1 or 11-beta HSD2.
20. The method of any of aspects 16 to 19, wherein the analyte comprises dehydroepiandrosterone.
21. The method of any of aspects 16 to 20, wherein t converting the analyte comprises enzymatically converting the analyte with an enzyme, the enzyme comprising sulfotransferase enzymes.
22. The method of any of aspects 16 to 21, wherein the metabolite comprises at least one of DHEA-S, 7α-hydroxy-DHEA, 7β-hydroxy-DHEA, 7-keto-DHEA, 7α-hydroxyepiandrosterone, 7β-hydroxyepiandrosterone, androstenediol, or androstenedione.
23. The method of any of aspects 16 to 22, wherein converting the analyte into the metabolite occurs in a fluid channel of a device, sensing the metabolite occurs in the fluid channel, and converting the analyte into the metabolite occurs upstream in the channel from sensing the metabolite.

What is claimed is:

1. A device for sensing an analyte in a sample solution comprising:
  a substrate;
  a conversion component that converts analyte in the sample solution into a metabolite, the conversion component positioned on the substrate;
  an aptamer sensor that can detect or measure a presence of the metabolite, the aptamer sensor located on the substrate;
  wherein the conversion component is chosen from:
    (i) a source of enzymes, the enzymes being able to metabolize the analyte, and
    (ii) a metabolic pathway, the metabolic pathway being able to metabolize the analyte.

2. The device of claim 1, wherein the analyte comprises a steroid hormone.

3. The device of claim 1, wherein the analyte comprises a drug molecule.

4. The device of claim 1, wherein the metabolite comprises at least one of cortisone, 5-alpha THF, 5-beta THF, or tetrahydrocortisone.

5. The device of claim 1, wherein the conversion component comprises at least one of 11-beta HSD1 or 11-beta HSD2.

6. The device of claim 1, further comprising an electronical supply in electrical communication with the aptamer sensor, the electrical supply configured to supply electrical power to the aptamer sensor.

7. The device of claim 1, wherein the aptamer sensor is housed by the conversion component and the substrate.

8. The device of claim 1, further comprising a fluid channel, wherein the conversion component and aptamer sensor are located in the fluid channel, the conversion component being upstream of the aptamer sensor.

9. The device of claim 1, wherein the conversion component is a coating placed on or adjacent to the aptamer sensor that is located in the fluid channel.

10. The device claim 1, wherein the analyte comprises dehydroepiandrosterone.

11. The device claim 1, wherein the conversion component comprises sulfotransferase enzymes.

12. The device of claim 1, wherein the metabolite comprises at least one of DHEA-S, 7α-hydroxy-DHEA, 7β-hydroxy-DHEA, 7-keto-DHEA, 7α-hydroxyepiandrosterone, 7β-hydroxyepiandrosterone, androstenediol, or androstenedione.

13. The device of claim 1, wherein the terminal half-life of the metabolite is between 7 to 10 hours, inclusively.

* * * * *